United States Patent [19]

Squirrell

[11] Patent Number: 5,750,337
[45] Date of Patent: May 12, 1998

[54] METHODS FOR DETECTING NUCLEIC ACID SEQUENCES USING EVANESCENT WAVE DETECTION

[75] Inventor: David J. Squirrell, Salisbury, Great Britain

[73] Assignee: The Secretary Of State For Defence In Her Britannic Majesty's Government Of The United Kingdom Of Great Britain And Northern Ireland, London, England

[21] Appl. No.: 196,185

[22] PCT Filed: Sep. 16, 1992

[86] PCT No.: PCT/GB92/01698

§ 371 Date: Feb. 23, 1994

§ 102(e) Date: Feb. 23, 1994

[87] PCT Pub. No.: WO93/06241

PCT Pub. Date: Apr. 1, 1993

[30] Foreign Application Priority Data

Sep. 16, 1991 [GB] United Kingdom ............... 9119735

[51] Int. Cl.⁶ .................................................. C12Q 1/68
[52] U.S. Cl. .................... 435/6; 435/91.2; 435/810; 436/501; 422/50; 422/68.1; 935/77; 935/78
[58] Field of Search ............................ 435/6, 4, 91.2, 435/91.21, 91.5, 91.51, 91.52, 174, 176, 287, 288, 291, 316, 808, 810; 436/501, 56, 46, 63; 536/22.1, 23.1, 24.1, 24.3, 24.31-33, 25.3, 25.32; 422/50, 52, 55, 57, 61, 68.1, 69, 82.05, 82.07, 82.08, 82.11; 935/77, 78, 88

[56] References Cited

U.S. PATENT DOCUMENTS

| H1398 | 1/1995 | Campbell | 435/6 |
|---|---|---|---|
| 4,582,809 | 4/1986 | Block et al. | 436/527 |
| 4,683,195 | 7/1987 | Mullis et al. | 435/6 |
| 5,242,797 | 9/1993 | Hirschfield | 435/6 |

FOREIGN PATENT DOCUMENTS

| 1000572 A | 2/1989 | Belgium . |
|---|---|---|
| 0 070 687 | 1/1983 | European Pat. Off. . |
| 0 144 914 | 6/1985 | European Pat. Off. . |
| 0 245 206 | 11/1987 | European Pat. Off. . |
| 0320308 | 6/1989 | European Pat. Off. . |
| 0 382 433 A3 | 8/1990 | European Pat. Off. . |
| 0 435 150 A2 | 7/1991 | European Pat. Off. . |
| 0 478 319 A1 | 4/1992 | European Pat. Off. . |
| 90/13666 | 11/1990 | WIPO . |
| 91/02981 | 3/1991 | WIPO . |

OTHER PUBLICATIONS

Graham et al Biosensors & Bioelectronics, 7 (1992) 487–493) Gene probe assays on a fibre–optic evanescent wave biosensor.

*Primary Examiner*—Ardin H. Marschel
*Attorney, Agent, or Firm*—Nixon & Vanderhye P.C.

[57] ABSTRACT

The present invention relates a method for the detection, identification and/or quantification of plant or animal tissues, microorganisms or cell free RNA or DNA and to detector apparatus adapted for performing said method. The method particularly uses Total Internal Reflection Fluorescence (TIRF) to measure hybridization of analyte RNA or DNA with RNA or DNA that is associated with an evanescent wave detector waveguide.

19 Claims, 5 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: DNA (genomic)

( x i ) SEQUENCE DESCRIPTION: SEQ ID NO:1:

CACGTTGTGG ACTGTTTGGA  20

( 2 ) INFORMATION FOR SEQ ID NO:2:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: DNA (genomic)

( x i ) SEQUENCE DESCRIPTION: SEQ ID NO:2:

TCCAAACAGT CCACAACGTG  20

( 2 ) INFORMATION FOR SEQ ID NO:3:

( i ) SEQUENCE CHARACTERISTICS:
- ( A ) LENGTH: 16 base pairs
- ( B ) TYPE: nucleic acid
- ( C ) STRANDEDNESS: single
- ( D ) TOPOLOGY: linear ( i i ) MOLECULE TYPE: DNA (genomic)

( x i ) SEQUENCE DESCRIPTION: SEQ ID NO:3:

CAACACACCT TAACAC  16

( 2 ) INFORMATION FOR SEQ ID NO:4:

( i ) SEQUENCE CHARACTERISTICS:
- ( A ) LENGTH: 16 base pairs
- ( B ) TYPE: nucleic acid
- ( C ) STRANDEDNESS: single
- ( D ) TOPOLOGY: linear ( i i ) MOLECULE TYPE: DNA (genomic)

( x i ) SEQUENCE DESCRIPTION: SEQ ID NO:4:

GTGTTAAGGT GTGTTG  16

( 2 ) INFORMATION FOR SEQ ID NO:5:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: DNA (genomic)

( x i ) SEQUENCE DESCRIPTION: SEQ ID NO:5:

CTTTAATTGT CGCGAGTGTT                                                                      20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AACACTCGCG ACAATTAAAG                                                                      20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AATTCAAGTA CGGTCGCAAT                                                                      20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AATTCAAGTA CGGTCGCAAT                                                                      20

METHODS FOR DETECTING NUCLEIC ACID SEQUENCES USING EVANESCENT WAVE DETECTION

This is a 371 filing of PCT/GB92/01698, filed Sep. 16, 1992.

The present invention relates a method for the detection, identification and/or quantification of plant or animal tissues, microorganisms or cell free RNA or DNA and to reagents and detector apparatus adapted for performing said method. The method particularly uses Total Internal Reflection Fluoresence (TIRF) to measure hybridization of analyte RNA or DNA with RNA or DNA that is associated with an evanescent wave detector waveguide.

Gene probe assays, using nucleic acid hybridization, are an alternative to immunoassays in the detection and identification of biological materials. The specificity of gene probes for their targets can be controlled much more easily than is possible using protein-based binding phenomena and, when coupled with the polymerase chain reaction to pre-amplify the target material, extreme sensitivity can be obtained. Current techniques using gene probes are slow, taking from hours to days to produce a result. Biosensors offer an alternative route to fast gene probe assays, but the only reports so far on gene probe biosensor assays are those using surface plasmon resonance (Evans & Charles (1990); Abstracts of 1st World Congress on DNA probes and immunoassay; Pollard-Knight et al (1990) Ann. Biol. Clin, 48 642–646).

Evanescent wave biosensors, which use the phenomenon of TIRF for detection (Sutherland & Dahne, (1987) J. Immunol. Meth., 74, 253–265), have previously been used with proteins as the biological recognition element. Antibodies have been used to detect the binding of fluorescent-labelled antigen (Eldefrawi et al (1991) Biosensors & Bioelectronics, 6, 507–516) using acetylcholine receptors to study the binding of acetylcholine and cholinesterase inhibitors. Other groups (Poglitsch & Thompson (1990) Biochemistry, 29, 248–254) have measured the binding of antibody to $F_c$ epitopes.

The present invention provides a method for carrying out gene probe assays with an evanescent wave biosensor and provides a TIRF waveguide which is adapted for carrying out said method when incorporated within an evanescent wave biosensor device.

Evanescent wave detectors exploit the TIRF phenomenon to provide a sensitive method for detecting reactions at the surface of waveguides. The waveguide may take various forms but typically will be a prism, slab or fibre. The reaction to be used to measure the target molecule may be monitored, for example, through measuring the fluorescence changes on binding or desorption of fluorescent species or by the generation of fluorescent species by enzymic or chemical means. Several patents have been published that cover the use of evanescent wave detectors with immunoassay systems as the biological sensing element (eg. U.S. Pat. No. 4,582,809) but the inherent limitations in the immunoreagents have not allowed the full capabilities of the sensor to be exploited.

The present invention provides a method for the detection, identification and/or quantification of a material selected fom plant or animal tissue, microorganisms or cell free RNA or DNA comprising:

(i) providing an oligonucleotide, complementary to all or part of an oligonucleotide sequence characteristic of the RNA or DNA of the material, immobilised on the surface of an evanescent wave detector apparatus waveguide;

(ii) exposing the immobilised oligonucleotide of step (i) to the sample, or DNA or RNA material derived therefrom, under conditions whereby DNA or RNA having the characteristic oligonucleotide sequence will hybridize with it;

(iii) associating the immobilised oligonucleotide of step (i) or the nucleic acid material derived from the sample with a fluorescently detectable agent, before, during or on completion of any hybridization with DNA or RNA as provided in step (ii), such that the fluorescently detectable agent becomes bound to the hybridized product but not to unhybridized immobilized oligonucleotide;

(iv) measuring the fluorescently detectable agent bound by step (iii) using the evanescent wave detector apparatus and relating the amount of that to the presence, identity and/or amount of the material.

In one preferred form of the present invention the fluorescently detectable agent is a fluorescently detectable intercalating dye capable of being incorporated into the duplex of the hybridization product. In this form of the method the dye is one that does not bind to the unhybridized immobilised oligonucleotides. Such method of determining the presence of hybridization product is ideally used with immobilised sequences of sufficient length in themselves to provide specific hybridization under the hybridization conditions used. The sample so analysed may be unaltered in DNA/RNA content, or may have had this enriched by specific sequence amplification, eg. polymerase chain reaction amplification (PCR) or ligase chain reaction (LCR).

In a second preferred form the fluorescently detectable agent is a fluorescently detectable oligonucleotide which is capable of hybridizing with the hybridized characteristic sequence or which is capable of acting as a specific sequence amplification primer, eg. such as a polymerase chain reaction primer, to yield fluorescently detectable amplification product, which is detectable using evanescence when hybridized to the waveguide immobilised oligonucleotide.

In a preferred embodiment of the second form, using detectable oligonucleotide, the present invention provides a method for the detection, identification and/or quantification of a material selected from plant or animal tissue, microorganisms or cell free RNA or DNA comprising:

(i) providing an oligonucleotide, complementary to part of an oligonucleotide sequence characteristic of the RNA or DNA of the material to be detected, immobilised on the surface of an evanescent detector apparatus waveguide;

(ii) providing a fluorescently detectable oligonucleotide complementary to all or part of the remainder of the characteristic sequence;

(iii) exposing the immobilised oligonucleotide from (i) to a solution comprising material to be investigated, or DNA or RNA material derived therefrom, under conditions whereby characteristic oligonucleotide sequence will hybridize with it;

(iv) replacing the solution of material from (iii) with a solution comprising the fluorescently detectable complementary oligonucleotide from (ii) and (v) measuring the amount of bound fluorescently detectable oligonucleotide using the evanescent wave detector apparatus and relating that to the presence, identity and/or amount of target material in the sample.

In a further preferred embodiment the present invention provides a method for the detection, identification and/or quantification of, plant or animal tissues, microorganisms or cell free RNA and DNA comprising:

(i) providing an oligonucleotide, complementary to part of an oligonucleotide sequence characteristic of the RNA or DNA of the material to be detected, immobilised on the surface of an evanescent wave detector apparatus waveguide;

(ii) providing a fluorescently detectable oligonucleotide identical to all or part of the remainder of the characteristic sequence;

(iii) performing a specific sequence amplification reaction on a sample of the material under investigation using the fluorescently detectable oligonucleotide of step (ii) as one of the primers, to thereby amplify any of the characteristic sequence present while incorporating fluorescently detectable agent therein;

(iv) exposing the waveguide immobilised complementary oligonucleotide of step (i) to the reaction mixture from step (iii) under conditions whereby hybridization of the amplification product with said immobilised oligonucleotide will occur;

(v) measuring any fluorescently detectable oligonucleotide hybridized with the immobilised oligonucleotide using the evanescent wave detector and relating that to the amount of amplified material initially present in the sample.

Preferably and conveniently the specific amplification reaction of step (iii) is a polymerase chain reaction, but other such reactions such as the ligase chain reaction may usefully be employed, as will be clear to those skilled in the art.

In all of the embodiments of the invention the waveguide is preferably situated within a temperature controllable environment, eg. within a temperature regulated chamber, such that the stringency of the hybridization of the complementary sequences to the target RNA or DNA may be controlled, or such that the polymerase chain reaction denaturation, hybridization and extension temperature cycles might be carried out.

The fluorescently detectable complementary oligonucleotides may be provided in a number of forms, eg. as an oligonucleotide tagged either with a fluorescent label, with a moiety to which a fluorescent species can be bound or with an enzyme or catalyst capable of generating fluorescent species. Thus step measuring steps may require additional steps prior to the basic fluoresence detection step, eg: exposure of the moiety to which a fluorescent species may be bound to such species or by exposure to substrate for the enzyme or catalyst reaction.

The complemetary sequence of step (i) may be of sufficient length to specifically bind the target RNA or DNA whilst leaving enough unbound target RNA or DNA sequence to bind the detectable oligonucleotide of step (iii). Typically the immobilised sequence will comprise about half of the length of the target sequence, but increasing the length of target sequence will allow lesser proportions to be used.

In a preferred embodiment employing the detectable oligonucleotide, the detectable sequence of will be complementary to all or almost all of the remainder of the target sequence but this may similarly be a reduced portion as target characteristic sequence length increases.

Advantageously the immobilised oligonucleotide is complementary to a sequence toward or at one end of the target sequence while the fluorescently detectable sequence is complementary to a sequence toward of at the other end. Thus restriction endonucleases may be conveniently employed prior to the hybridization for the purpose of cleaving the RNA or DNA of the sample material in order to allow easier access to these ends of the characteristic target sequence. Similarly in the second preferred embodiment the detectable sequence need only be long enough to be useful as a PCR primer of the necessary specificity but may be longer. It will be appreciated that both PCR primers may be fluorescently detectable thus increasing the potential fluorescence provided at the waveguide surface and thus the efficacy corresponding evanescent effect. In all cases preferred reagent baselengths are 5–30, more preferably 10–25, eg. 15–20 bases.

It will be realised by the man skilled in the art that the complementary sequences need not be complemetary at every base pair where they hybridize. Thus a man skilled in the art will readily determine the stringency requirements for statistically acceptable use of mismatched oligomers eg. 90% complementary sequences and will be able to obtain usable results by adjusting the hybridization temperature accordingly where such mismatched sequences are used.

The requirements for precise complementary sequence usage will vary with the uniqueness of the sequence for which the user is assaying. Thus a sequence that shares a high percentage of bases with other potentially present sequences will require use of a more completely complementary sequence than a sequence that is relatively distinct. Thus where the sequence being assayed for is not fully elucidated or is variable, the skilled man may be able to determine statistically acceptable oligomers for steps (i) and (iii).

A second aspect of the present invention provides an assay kit for use in the method of the invention comprising:

(1) an oligonucleotide complementary to all or part of an oligonucleotide sequence characteristic of the RNA or DNA of the material to be detected and (2) a fluorescently detectable oligonucleotide complementary or identical to part or all of the remainder of the characteristic sequence.

The options for the components (1) and (2) are those which are set out above and in the claims, these components being optionally supplemented in the kit by those reagents necessary for immobilisation of the oligomer (1) on the waveguide; examples of suitable reagents being those referred to in the discussion of methods below.

A third aspect of the invention provides a waveguide suitable for use in an evanescent wave biosensor characterised in that it comprises, immobilised upon its surface, an oligonucleotide which is complementary to all or part of an oligonucleotide sequence which is characteristic of the RNA or DNA sequence of the material which is to be detected. Furthermore kits comprising such waveguides are provided for use in the method of the invention, as set out in the claims.

In a fourth aspect of the present invention is provided an evanescent wave detector biosensor characterised in that it comprises a waveguide which has, immobilised upon its surface, an oligonucleotide which is complementary to all or part of an oligonucleotide sequence which is characteristic of the RNA or DNA sequence of the material which is to be detected. Such waveguide may eg. be a prism, slab or fibre.

In all of the aspects of the invention, it will be realised that more than one characteristic sequence may be targeted simultaneously by employing more than one type of immobilised oligonucleotide and associated fluorescently detectable binding agent in the method and apparatus used to carry it out.

Advantages of the present method over analogous immunoassay systems include:

(a) denser packing of the immobilised component on the waveguide surface allowing greater sensitivity and dynamic range and making the construction of multi-specificity surfaces easier;

(b) the binding between the analyte and the immobilised and derivatised oligonucleotides can be regulated by adjusting the hybridization conditions and the lengths of the oligonucleotides, thus permitting the specificity and sensitivity of a given test to be finely adjusted to suit requirements;

(c) immunoassays are limited by availability of reagents, stability of reagents, antigenic variability, masking of antigenic sites, and the dissociation constants of the antibody/antigen complexes. Gene probe assays are potentially superior in all these respects;

(d) fluorescent immunoassays suffer from interference from environmental contaminants and non-specific binding while the higher temperatures required for gene probe assays (ie. above 60° C. rather than 37° C.) will reduce unwanted adsorption of contaminants on the detector surface;

(e) as a result of the lower dissociation constants obtainable with nucleic acid complexes compared with immune complexes the full sensitivity of evanescent wave detector technology can be realised.

The samples to be investigated may be as found in the environment (eg. for free RNA or DNA oligonucleotides) or may be pretreated such as by cell lysis techniques, DNA/RNA concentration or amplification (eg. as by polymerase chain reaction using Taq polymerase) or by restriction enzyme mediated degredation (eg. to provide more manageable sized oligonucleotides).

The potential of the method, kits and apparatus of the present invention will now be illustrated by way of example only with reference to the following Figures and Experiments; further embodiments will occur to the skilled man in the light of these.

FIGURES

FIG. 1: shows the principal elements of the evanescent wave detector used in the Examples.

FIG. 2: shows the volt age/time relationship obtained on hybridization of a fluorescein-labelled 20-mer with a complementary sequence covalently coupled to an optic fibre waveguide.

FIG. 3: shows concentration/response curves showing specific hybridization of complementary and control oligonucleotides; signal (mV/min) plotted against nM concentration oligomer.

FIG. 4: shows the effect of flow rate of sample solution throught the temperature controlled chamber containing the waveguide on the hybridization signal; signal (mV/min) is plotted against flow rate (ml/min).

FIG. 5: shows the influence of temperature on the rate of hybridization; signal (mV/min) is plotted against temperature °C. for a 50 ng/ml sample of a fluorescein labelled 20-mer.

FIG. 6: shows a pH profile of oligonucleotide hybridization on the optic fibre waveguide; signal (mV/min) plotted against pH.

FIG. 7: shows binding from 8 nM solutions of oligomers complementary to the proximal or distal ends of a covalently coupled 204 base oligonucleotide.

Figure 8A:
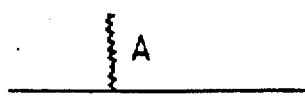
FIG. 8a depicts an oligonucleotide sequence (A) complementary to part of an oligonucleotide sequence characteristic of a target DNA sequence (B) immobilized upon an evanescent wave detector waveguide.
Figure 8B:
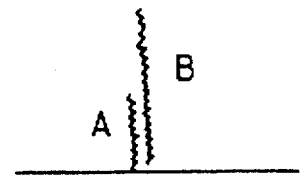
FIG. 8b depicts the immobilized oligonucleotide exposed under hybridization conditions to a solution of sample under investigation and target DNA sequence (B) therein hybridizes to sequence (A)
Figure 8C:
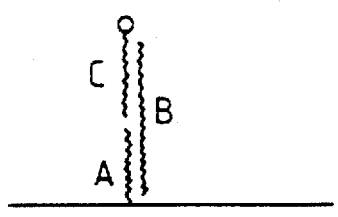
FIG. 8c depicts the sample solution replaced with a solution comprising a fluorescein labeled oligonucleotide (C) which is complementary to the unhybridized remainder of the target oligonucleotide, also under hybridizing conditions, and this is similarly hybridized. On hybridization the fluorescein is caused to fluoresce by the light in the evanescent zone of the waveguide.
Figure 8D:
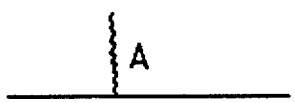
FIG. 8d shows the complementary sequence (A) immobilized upon an evanescent wave detector waveguide.
Figure 8E:
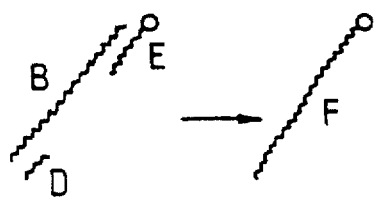
Figure 8F:
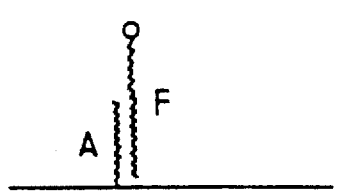
Figure 8H:
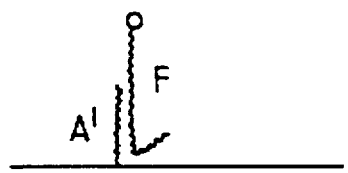

FIG. 8e depicts a sample solution treated under PCR conditions with two primers (D) and (E), each corresponding to a characteristic sequence at one of the two ends of the target characteristic sequence (B). The primer for the end of the sequence which is opposite to the end which hybridizes to the immobilized oligonucleotide (A) is labeled with fluorescein and thus a product of the reaction is fluorescein labeled target sequence (F); and FIGS. 8f and 8h depict immobilized sequence (A) exposed to the sample solution under hybridization conditions wherein fluorescein labeled target sequence (F) hybridized to the sequence (A) may be detected by the evanescent wave detector induced fluorescence.

METHODS

Since oligonucleotides are long-chain molecules with lengths that can be comparable to the depth of the evanescent zone, studies were carried out which hybridized short, fluorescein-labelled oligonucleotides to either end of a 204-base oligomer, a fragment amplified from protective antigen gene of *Bacillus anthracis*, tethered at one end to the waveguide surface to examine the influence of probe length on detection.

Materials

Glutaraldehyde, 3-aminopropyl triethoxysilane (APTS), Tween 20, Ficoll, formamide, polyvinyl pyrrolidone, bovine serum albumin fraction V (BSA), horse radish peroxidase labelled streptavidin (HRP-SA), 2,2,-azino-bis(3-ethylbenzthiazoline-6-sulphonic acid) (ABTS), sodium chloride and trisodium citrate were obtained from the Sigma Chemical Company, Poole, UK. Sodium dihydrogen orthophosphate, disodium hydrogen orthophosphate, sodium dodecyl sulphonate (SDS), hydrogen peroxide, hydrochloric acid, and acetone were AR grade from BDH, Poole, UK. Ammonium hydroxide was obtained from Aldrich, Gillingham, Dorset, UK and ethanol from Hayman Ltd., Witham, Essex, UK. Streptavidin immobilised on agarose beads was obtained from Pierce and Warriner, Chester, UK. Synthetic DNA oligonucleotides with C6-linked fluorescein-, amino- or biotin-modified ends were purchased from British Bio-Technology Ltd, Abingdon, UK are listed in Table 1.

TABLE 1

Oligonucleotides Used (5' to 3')

| ID No. | Sequence |
|---|---|
| SEQ ID NO: 1 | CACGTTGTGGACTGTTTGGA-amino |
| SEQ ID NO: 2 | TCCAAACAGTCCACAACGTG-fluorescein |

TABLE 1-continued

Oligonucleotides Used (5' to 3')

| ID No. | Sequence |
| --- | --- |
| SEQ ID NO: 3 | CAACACACCTTAACAC-amino |
| SEQ ID NO: 4 | GTGTTAAGGTGTGTTG-fluorescein |
| SEQ ID NO: 5 | Amino-CTTTAATTGTCGCGAGTGTT |
| SEQ ID NO: 6 | Fluorescein-AACACTCGCGACAATTAAAG |
| SEQ ID NO: 7 | Biotin-AATTCAAGTACGGTCGCAAT |
| SEQ ID NO: 8 | Fluorescein-AATTCAAGTACGGTCGCAAT |

Figure 1:
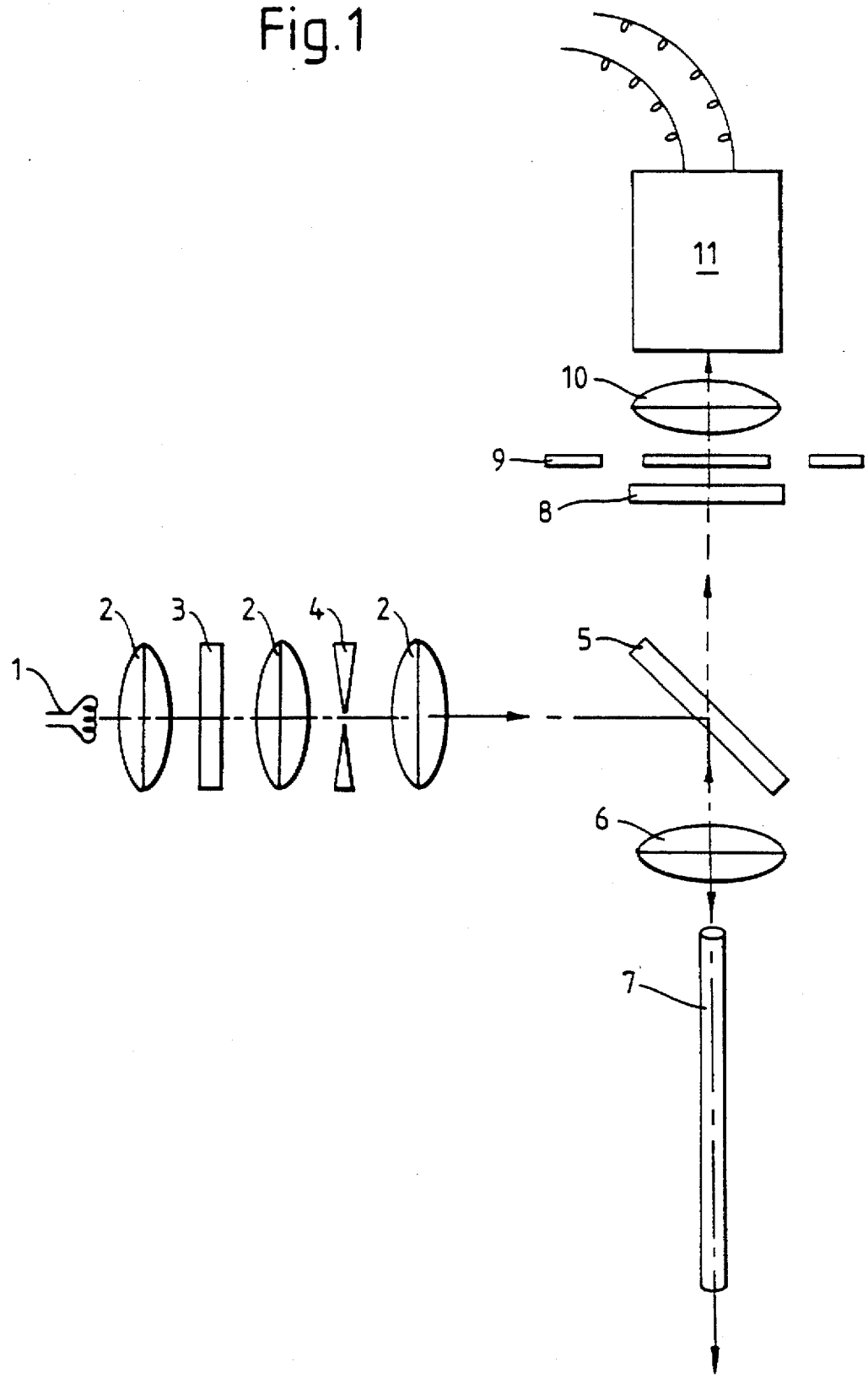

The fibre optic evanescent wave device, (prototype No.19), and 1 mm=65 mm quartz optic fibres were purchased from ORD, North Salem, N.H., USA. See FIG. 1. A six watt tungsten filament source (1) provides light which is passed through three collimating lenses (2) interspaced by a 485 mm blue filter (3) and a 0.8 mm pinhole mask (4) to impinge upon a 50:50 beam splitting device (5) which intermittently directs light through a focussing lens (6) and into the oligonucleotide bearing waveguide (7). Fluorescent light derived from any bound, eg. hybridized or intercalated, fluorescent material responding to the incoming light is redirected out of the waveguide (7) via the lens (6) and is allowed to pass through the beam splitting device toward a 530 nm green filter (8). From here light passes through a shutter assembly (9) and a focussing lens (10) whereafter it impinges upon a detector device (11) connected to a measuring device such as a voltmeter (not shown).

The output voltage from the voltmeter is conveniently connected to a Pharmacia model 482 chart recorder. Optic fibres were held in a jacketed flow cell constructed from glass capillary tubing with stainless steel end caps and silicone gaskets. Temperature was controlled by circulating water from a water bath through the glass jacket. The temperature was monitored using a thermocouple. Optic fibres were cleaned and then covalent coupling with glutaraldehyde was carried out using a method based on that described by Tijssen, (1985), Practice and theory of enzyme immunoassays: page 322 to 323 of Vol 15 of Laboratory Techniques in Biochemistry and Molecular Biology. Ed: Burdon and van Knippenburg: Pub. Elsevier.

Fibres were silanised in a 2% solution of APTS in acetone for 24 hrs at room temperature, washed with acetone, dried at 50° C., immersed in 1% glutaraldehyde in water for 1 hour, washed in PBS and finally left overnight at 4° C. in a 10 ug/ml solution of oligonucleotide with an aminoterminal. To perform an assay an optic fibre with immobilised oligonucleotide was rinsed in deionised water, blotted dry and inserted into the flow cell. When optimised, the following conditions, adapted from Anderson & Young, (1985) Nucleic acid hybridization—a practical approach Ed. Hames and Higgins; IRL Press, Oxford, pp 73–111, were used. The temperature of the water jacket was adjusted to 65° C.

Prehybridisation solution, (250 ml 20×SSC, plus 50 ml 100×Denhardt's solution, 50 ml 0.1 M phosphate buffer and 1 ml Tween 20 added to 600 ml sterile deionised water, final pH 6.8) was pumped using a peristaltic pump over the fibre in the 25 µl flow cell at 0.5 ml/min until a steady baseline was obtained. The fluorescein end-labelled target oligonucleotide, in prehybridization solution, was then introduced at the same flow rate and hybridization was followed as the increase in output on the chart recorder. After a few minutes prehybridization solution was switched back into the flow cell and the temperature raised to 80° C. After 10 to 15 minutes all the bound oligonucleotide had desorbed and the temperature was lowered to 65° C. ready for another run.

Initially only short (16- to 20-mer) oligonucleotides were attached to the fibres. To investigate the use of longer probes an amino-ended 204-mer was synthesised using PCR on the target sequence with one primer, a 20-mer, end-labelled with an amino-group—oligo.5453—and the other primer, also a 20-mer, end-labelled with biotin oligo.1222. Unincorporated amino-labelled primer was removed using streptavidin immobilised on agarose beads to pull out double-stranded PCR product from unincorporated amino-ended primer. The amino-labelled 204-base strand was released from the complementary strand and the beads by heating at 95° C. for 10 minutes followed by quick chilling in a water/ice mixture and then removing the beads by centrifugation. The amount of the 204-mer produced was sufficient for a 0.85 µg/ml solution to be used for coupling to fibres.

Assay Of Oligomers

In initial 20-mer experiments high levels of target and control oligonucleotides were used. A 200 nM (1 µg/ml) solution of fluorescein-labelled oligonucleotide control (oligo.4950) was introduced at 1 ml/min and 60° C. into the flow cell containing a fibre with .oligo.4946 immobilised. There was an immediate shift in baseline of 80 mV whereafter the output remained constant until prehybridisation solution was reintroduced when the output returned to its previous level. In contrast, when oligo.4947 which was complementary to oligo.4946 on the fibre was introduced at 160 nM. (also 1 µg/ml), a continuously rising signal was obtained with an initial slope of about 350 mV/min. A plateau was reached after 14 minutes at an output 1,140 mV above the baseline level. The output fell again when prehybridization solution at 90° C. was passed through the flow cell. To confirm that binding was specific, the control oligo.4950 was shown to bind to an optic fibre with its complement, oligo.4949, covalently coupled to the surface.

Figure 2:
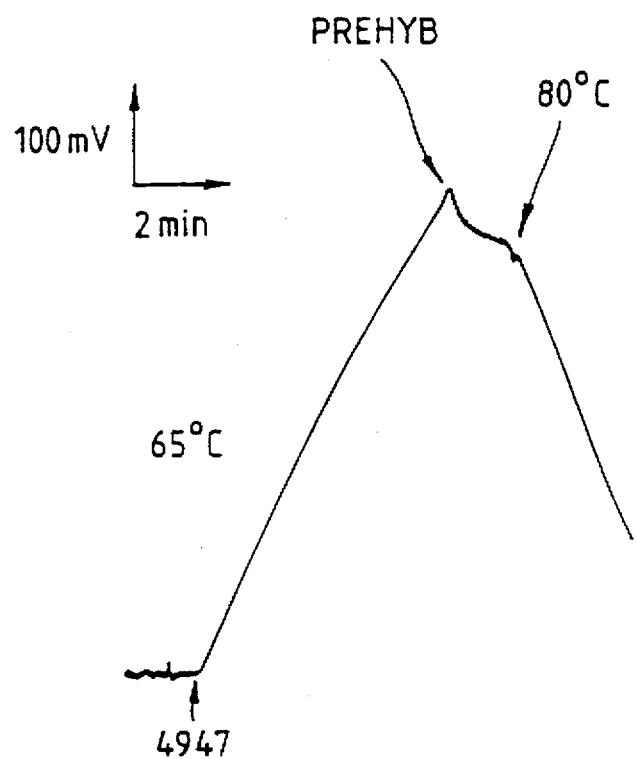
Figure 3:
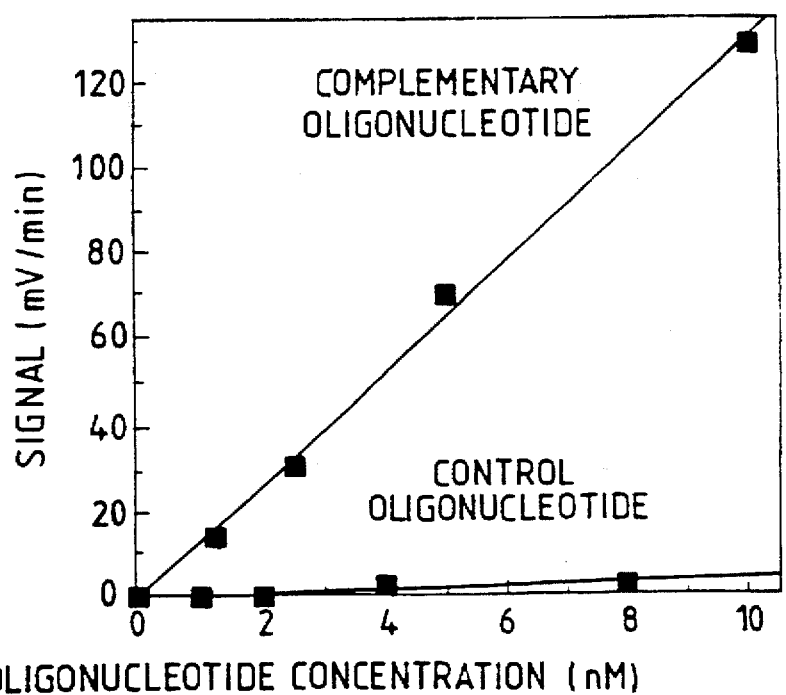

The time course of hybridization of 8 nM fluorescein-labelled oligo.4947 to immobilised oligo.4946 is shown in FIG. 2 and a concentration/response curve for fluorescein-labelled oligo.4950 hybridizing to immobilised oligo.4949 with oligo.4947 as a control is given in FIG. 3. The slopes of the curves were measured 1 minute after sample entered the flow cell.

Figure 4:
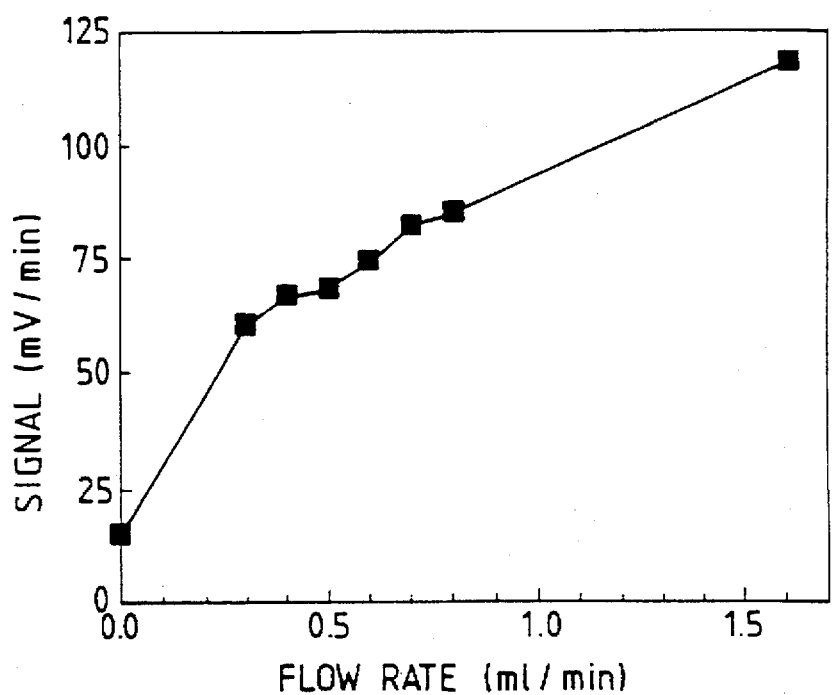
Figure 5:
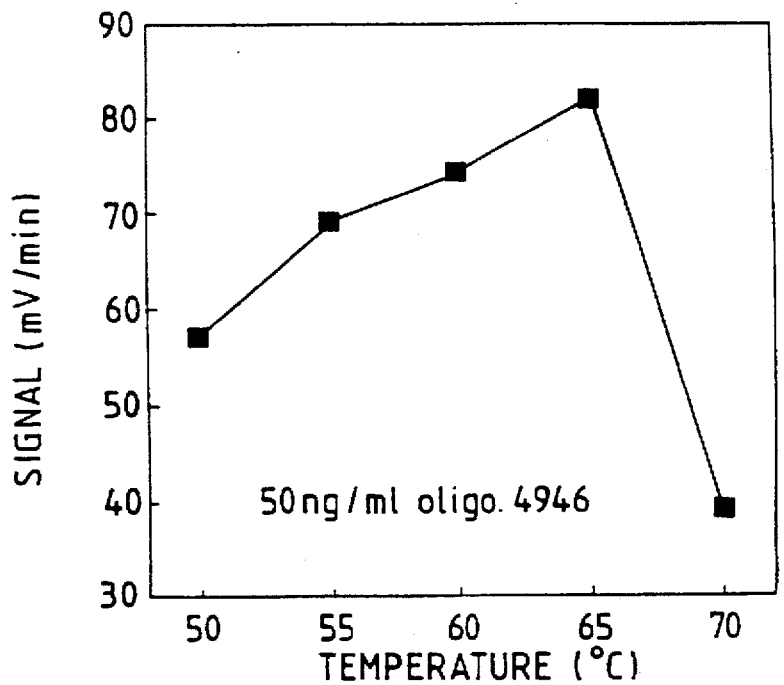
Figure 6:
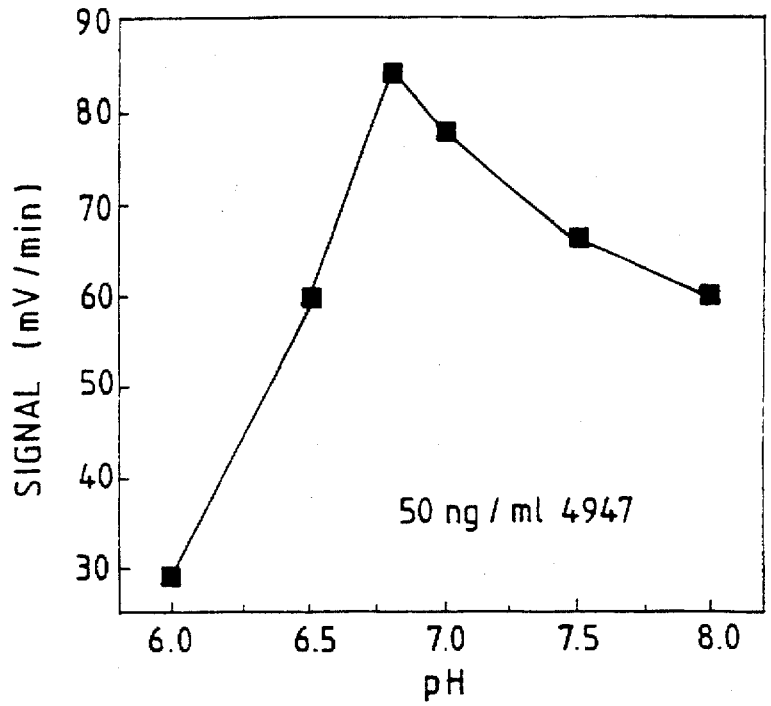

Results from the optimisation of conditions are shown in FIGS. 4–6. The effect of flow rate was evaluated with 50 ng/ml solutions of oligo.4947. The results are shown in FIG. 4. The dependence of the rate of hybridization on temperature and pH were evaluated and the results are shown in FIGS. 5 & 6, respectively. Maximum rates of binding were observed at 65° C. and pH6.8.

Figure 7:
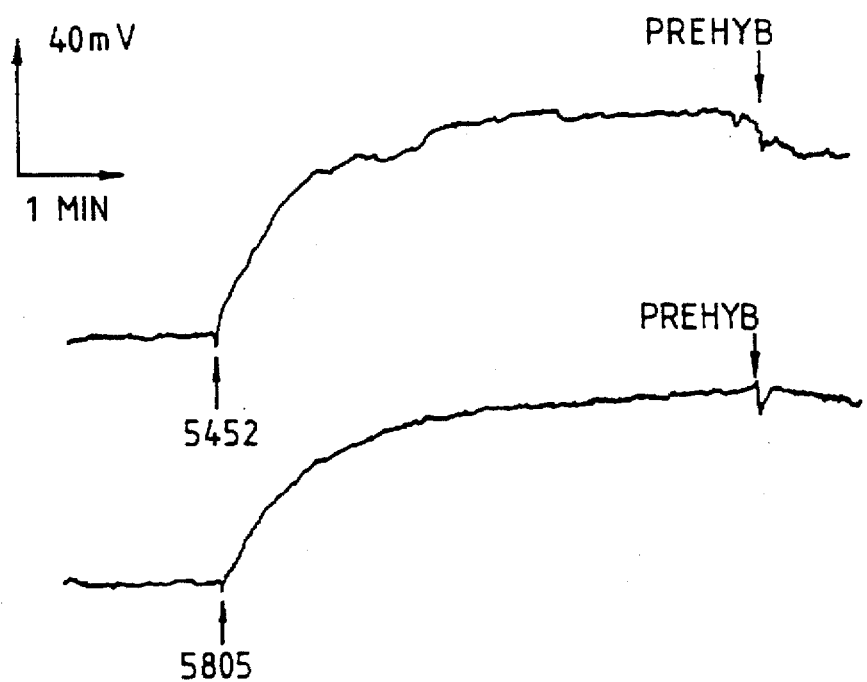

The binding curves of 50 nM solutions of fluorescein-labelled oligonucleotides complementary to either the proximal or distal ends of a 204-base oligonucleotide covalently coupled at one end to the waveguide surface are shown in FIG. 7. There was little difference between responses with both showing a rapid rise to a plateau level of 48 mV (proximal) or 56 mV (distal) after about three minutes followed by a slight fall in output when prehybridisation solution was reintroduced into the flow cell. Concentration/response curves using initial slopes for hybridization of the two oligonucleotides showed little difference between them, (results not shown). Oligo.4947 at 500 nM as a control did not bind to the 204-mer.

Detection was in the nanomolar range with a linear relationship between the slope of the response and concentration: similar to results obtained using immunoassays with this biosensor.

For assays that require high sensitivity, the following equipment improvements and enhancement techniques are conveniently made:

Labelled oligomers are made using oligonucleotides labelled with multiple fluorophores or fluorescent beads, or fluorescent intercalating dyes are used to detect hybridization;

The biosensor assay may is combined with a DNA amplification technique such as PCR which could be performed on the sample, prior to the hybridization on the waveguide, preferably using fluorophore-labelled primers (as in one of the preferred embodiments of the method of this invention above) to improve detection of product. It would also be possible directly to monitor PCR reactions using the biosensor. The 60 seconds or so taken for the biosensor assays is orders of magnitude faster than conventional gene probe assays and still much faster than, rapid, tests that take about 1 hour to perform, (Engleberg,(1991) ASM News 57 (4) 183–186).

The easy recycling of the detector surface through removal of bound nucleic acids by heating obviates one of the problems encountered with immunoassays on this system and renders it, with the 60 second response period, useful in military or other critically hazardous environments requiring rapid identification. Several optic fibres were found to be usable over periods of several days with no loss in response.

Both 5' and 3' B,-labelled oligonucleotides were used with this factor had no apparent effect on the results. Oligonucleotides were also bound to the proximal and distal ends of a 204-base oligonucleotide. The length of this could have been from 70 nm, (using the value of 3.4 nm for the pitch of double-stranded DNA which has 10 bases per helical), to 200 nm, (using the inter-bond distances of the —O—P—O—C—C—C— repeats along the backbone of the molecule). The depth of the evanescent zone defined as the distance taken for the light intensity to fall to 1/e of its initial value would have been around 100 nm, comparable to the length of the 204-mer. Since similar signals were obtained for the hybridisation of distal and proximal fluorescein-labelled oligonucleotides, (slightly higher signals were obtained for the distal oligonucleotide), the orientation of the long oligonucleotide strands was presumably not perpendicular to the wave guide surface.

Only a limited amount of the 204-mer, which was generated by PCR from a larger target sequence, was available for coupling to the optic fibres and this presumably led to the concentration on the waveguide surface being relatively low. This would explain the rapid plateauing of the responses seen in FIG. 7 compared to the continuing rise in signal over an equivalent timescale seen in FIG. 2, (where the immobilised gene probe was at a higher concentration, being covalently coupled from a solution >100× more concentrated. If plateau height rather than rate of change of output were to be chosen as the measure of binding then limiting the amount of immobilised probe would allow saturation to be more rapidly achieved.

The molecular basis of the invention is provided in FIG. 8 wherein 8a–c and 8d–f refer to the first and second preferred embodiments of the method of the invention respectively. In 8a an oligonucleotide sequence (A) complementary to part of an oligonucleotide sequence characteristic of a target DNA sequence (B) has been immobilised upon an evanescent wave detector waveguide by the method described above. In 8b the immobilised oligonucleotide is exposed under hybridization conditions to a solution of sample under investigtion and target DNA sequence (B) therein hybridizes to sequence (A). In 8c the sample solution is replaced with a solution comprising a fluorescein labelled oligonucleotide (C) which is complementary to the unhybridized remainder of the target oligonucleotide, also under hybridizing conditions, and this is similarly hybridized. On hybridization the fluorescein is caused to fluoresce by the light in the evanescent zone of the waveguide.

In 8d the complementary sequence (A) is immobilised upon an evanescent wave detector waveguide as before; in 8e a sample solution is treated under PCR conditions with two primers (D) and (E), each corresponding to a characteristic sequence at one of the two ends of the target characteristic sequence (B). The primer for the end of the sequence which is opposite to the end which hybridizes to the immobilized oligonucleotide (A) is labelled with fluorescein and thus a product of the reaction is fluorescein labelled target sequence (F). In 8f immobilised sequence (A) is exposed to the sample solution under hybridization conditions wherein fluorescein labelled target sequence (F) is hybridized to the sequence (A) may be detected by the evanescent wave detector induced fluorescence.

In a preferred form of the method of FIGS. 8, particular to use with PCR or other specific amplification technique incorporating method, the immobilised oligonucleotide (A) is selected such that it is not capable of binding to the primers (D) and (E), thus excess of these will not result in a blocking of the immobilised site. Thus in this form olignucleotide (A') hybridizes to a portion of (F) more central in sequence (B) than primer (D) with the result that the non-fluorophor bearing end of (F) is as shown in FIG. 8h.

The intercalating dye utilising embodiments of the method of the invention whilst not specifically exemplified herein, are carried out as illustrated best by FIGS. 8a and 8b wherein these steps are carried out in the presence or with later addition of the dye. Suitable dyes and conditions for their interaction are disclosed in the prior art, eg. Latt and Wohlleb; Chromosoma (Berl.) 52, 297–316 (1975), Jorgenson et al. Chrmosoma (Berl.) 68, 287–302 (1978) and Jennings and Ridler; Biophysics of Structure and Mechanism, 10, 71–79, (1983).

TABLE 1

| Oligonucleotides Used (5' to 3') | |
|---|---|
| SEQ ID NO: 1 | CACGTTGTGGACTGTTTGGA |
| SEQ ID NO: 2 | TCCAAACAGTCCACAACGTG |
| SEQ ID NO: 3 | CAACACACCTTAACAC |
| SEQ ID NO: 4 | GTGTTAAGGTGTGTTG |
| SEQ ID NO: 5 | CTTTAATTGTCGCGAGTGTT |
| SEQ ID NO: 6 | AACACTCGCGACAATTAAAG |
| SEQ ID NO: 7 | AATTCAAGTACGGTCGCAAT |
| SEQ ID NO: 8 | AATTCAAGTACGGTCGCAAT |

I claim:

1. A method for the detection, identification or quantification of a material selected from plant or animal tissue, microorganisms or cell free RNA or DNA, said method comprising the steps of:
   (i) immobilizing an oligonucleotide, which specifically binds to all or part of a nucleotide sequence characteristic of the RNA or DNA of the material, on the surface of an evanescent wave detector apparatus waveguide;
   (ii) subjecting a sample of said material or RNA or DNA derived therefrom in solution to a sequence specific amplification in which a sequence comprising said sequence characteristic of the RNA or DNA of the material is amplified, the amplification being effected in contact with the immobilized oligonucleotide of step (i);
   (iii) during and/or on completion of the sequence specific amplification, subjecting the reaction mixture of step (ii) to conditions whereby DNA or RNA having the characteristic nucleotide sequence will hybridize with said immobilized nucleotide of step (i);
   (iv) during or on completion of the hybridization reaction in step (iii) associating any hybrid produced with a fluorescently detectable agent such that the fluorescently labeled agent becomes specifically bound to said hybrid but not to unhybridized immobilized oligonucleotide; and
   (v) measuring the fluorescently detectable agent bound by step (iv) using the evanescent wave detector apparatus and relating the amount of that to the presence, identity and/or amount of the material.

2. A method as claimed in claim 1, wherein the fluorescently detectable agent is a fluorescently detectable intercalating dye capable of being incorporated into a double stranded portion of any hybrid produced in step (iii), that being a dye that does not bind to unhybridized immobilized oligonucleotide of step (i).

3. A method as claimed in claim 1, wherein the specific sequence amplification is by polymerase chain reaction amplification (PCR) or ligase chain reaction (LCR).

4. A method as claimed in claim 1, wherein the fluorescently detectable agent is a fluorescently detectable oligonucleotide which is capable of hybridizing with a single stranded portion of any hybrid produced in step (iii).

5. A method for the detection, identification or quantification of a material selected from plant or animal tissue, microorganisms or cell free RNA or DNA, said method comprising the steps of:
   (i) immobilizing an oligonucleotide, which specifically binds to part of an oligonucleotide sequence characteristic of the RNA or DNA of the material to be detected, on the surface of an evanescent wave detector apparatus waveguide;

(ii) subjecting a sample of said material or RNA or DNA derived therefrom in solution to a sequence specific amplification in which a sequence comprising said sequence characteristic of the RNA or DNA of the material is amplified, the amplification being effected in contact with the immobilized oligonucleotide of step (i);

(iii) subjecting the reaction mixture of step (ii) to conditions whereby DNA or RNA having the characteristic immobilizing nucleotide sequence will specifically hybridize with said immobilized nucleotide of step (i);

(iv) replacing the solution of material present at the end of step (iii) with a solution comprising a fluorescently detectable complementary oligonucleotide which specifically binds to all or part of the remainder of the characteristic sequence; and (v) measuring the amount of bound fluorescently detectable oligonucleotide using the evanescent wave detector apparatus and relating that to the presence, identity and/or amount of said material in the sample.

6. A method as claimed in claim 5, wherein the temperature is controlled such that the stringency of the hybridization reaction between said characteristic oligonucleotide sequence and said immobilized oligonucleotide may be controlled, or such that the sequence specific amplification is effected.

7. A method as claimed in claim 5, wherein the immobilized oligonucleotide of (i) is from 5 to 30 bases long.

8. A method as claimed in claim 7, wherein the immobilized oligonucleotide is from 10 to 25 bases long.

9. A method as claimed in claim 8, wherein the immobilized oligonucleotide is 15 to 20 bases long.

10. A method for the detection, identification or quantification of a material selected from plant of animal tissue, microorganisms or cell free RNA or DNA, said method comprising the steps of:

(i) immobilizing an oligonucleotide, which specifically binds to all or part of a nucleotide sequence characteristic of the RNA or DNA of the material, on the surface of an evanescent wave detector apparatus waveguide;

(ii) subjecting a sample of said material or RNA or DNA derived therefrom in solution to a sequence specific amplification in which a sequence comprising said sequence characteristic of the RNA or DNA of the material is amplified and at the same time, becomes specifically associated with a fluorescently detectable agent, the amplification being effected in contact with the immobilized oligonucleotide of step (i);

(iii) during and/or on completion of the sequence specific amplification, subjecting the reaction mixture of step (ii) to conditions whereby the amplified product of step (ii) will specifically hybridize with said immobilized nucleotide of step (i); and (iv) measuring the fluorescently detectable agent bound by step (iii) using the evanescent wave detector apparatus and relating the amount of that to the presence, identity and/or amount of the material.

11. A method according to claim 10, wherein the fluorescently detectable agent is a fluorescently detectable oligonucleotide which is capable of specifically hybridizing with a part of the characteristic sequence.

12. A method according to claim 10, wherein the fluorescently detectable oligonucleotide is capable of acting as a primer in the said sequence specific amplification.

13. A method according to claim 12, wherein the said primer is a polymerase chain reaction primer.

14. A method as claimed in claim 1 or claim 5 or claim 10, wherein the waveguide comprises a prism, slab or fiber.

15. A method as claimed in claim 1, or claim 5 or claim 10, wherein the waveguide is situated within a temperature controllable environment.

16. A method as claimed in claim 15, wherein said environment is a temperature regulated chamber.

17. A method as claimed in claim 1 or claim 5 or claim 10, wherein the fluorescently detectable agent is provided by tagging an oligonucleotide either with a fluorescent label, or with a moiety to which a fluorescent species can be bound or with an enzyme or catalyst capable of generating fluorescent species.

18. A method as claimed in claim 17, wherein the fluorescently detectable agent comprises a specific sequence amplification primer which is used in step (ii), to yield fluorescently detectable amplification product, which is detectable by evanescence when hybridized to the immobilized oligonucleotide.

19. The method of claim 18, wherein the specific sequence amplification primer is a polymerase chain reaction primer.

* * * * *